(12) United States Patent
Sasaki et al.

(10) Patent No.: US 7,160,014 B2
(45) Date of Patent: Jan. 9, 2007

(54) ADJUSTMENT MECHANISM

(75) Inventors: Masahiko Sasaki, Chiba-ken (JP); Kohei Tsuchidate, Tokyo (JP)

(73) Assignee: PENTAX Corporation, Tokyo (JP)

( * ) Notice: Subject to any disclaimer, the term of this patent is extended or adjusted under 35 U.S.C. 154(b) by 127 days.

(21) Appl. No.: 11/071,240

(22) Filed: Mar. 4, 2005

(65) Prior Publication Data

US 2005/0197532 A1    Sep. 8, 2005

(30) Foreign Application Priority Data

Mar. 5, 2004 (JP) ............................. 2004-062043

(51) Int. Cl.
*A61B 1/06* (2006.01)
(52) U.S. Cl. ..................................... 362/574
(58) Field of Classification Search ................. 362/574
See application file for complete search history.

(56) References Cited

U.S. PATENT DOCUMENTS

| | | | |
|---|---|---|---|
| 6,099,466 A | 8/2000 | Sano et al. | |
| 6,482,150 B1 * | 11/2002 | Utsui | 600/178 |
| 6,602,186 B1 | 8/2003 | Sugimoto et al. | |
| 7,087,014 B1 * | 8/2006 | Sasaki | 362/574 |
| 2002/0175993 A1 | 11/2002 | Ueno et al. | |
| 2003/0219201 A1 | 11/2003 | Arimoto et al. | |

* cited by examiner

*Primary Examiner*—Ali Alavi
*Assistant Examiner*—William J Carter
(74) *Attorney, Agent, or Firm*—Greenblum & Bernstein, P.L.C.

(57) ABSTRACT

An adjustment mechanism that adjusts an inclination and a position of an optical axis of an excitation light optical system with respect to an optical axis of a white light optical system is provided. The adjustment mechanism includes a frame plate, a plate-shaped lever, a fixing unit, a first adjuster, and a second adjuster. The frame plate is orthogonally placed with respect to the optical axis of the white light optical system, and perforated with a pair of circular holes, and an elliptical hole. The plate-shaped lever is perforated with a first elliptical hole and a second elliptical hole and a cylindrical projection. The fixing unit fixes the excitation light optical system to the plate-shaped lever. The first adjuster includes a first supporting axle and a first disc-shaped cam to which the first supporting axle is eccentrically fixed, the first disc-shaped cam being rotatably and slidably fitted in the first elliptical hole of the plate-shaped lever. The second adjuster includes a second supporting axle and a second disc-shaped cam to which the second supporting axle is eccentrically fixed, the second disc-shaped cam being rotatably and slidably fitted in the second elliptical hole of the plate-shaped lever.

7 Claims, 10 Drawing Sheets

ADJUSTMENT MECHANISM

BACKGROUND OF THE INVENTION

The present invention relates to an adjustment mechanism that adjusts an inclination and a position of an optical axis of an optical system.

It is known that a body tissue is excited and emits a fluorescence when irradiated by light of a specific wavelength. An abnormal body tissue having a lesion such as a tumor or a cancer emits a weaker fluorescence than a normal body tissue does. Such reaction is also performed by a body tissue under a body cavity wall. Accordingly, an endoscope system that detects an abnormality in a body tissue under a body cavity wall utilizing such reactive phenomenon has recently been developed. Such an endoscope system is disclosed in, for example, U.S. Patent Application Publication No. 2002175993A1 and U.S. Pat. No. 6,602,186.

Functions of such endoscope systems include, in addition to a basic observation mode of simply emitting visible light from a tip of the endoscope to illuminate an internal area of a body cavity, a special observation mode of alternately emitting from the tip of the endoscope a visible light and an excitation light for exciting a body tissue under a body cavity wall.

SUMMARY OF THE INVENTION

FIG. 10 shows one example of a light source unit configured to be used in the endoscope system having the functions of the basic observation mode and the special observation mode.

In the basic observation mode, a light source unit of the endoscope system introduces white light emitted by a white light emitting device to a facet of a light guide fiber bundle extended through inside the endoscope. In the special observation mode, an optical path merging device is disposed in the optical path of the white light, and an excitation light emitting device provided in the light source unit emits excitation light to the optical path merging device, thus to introduce the excitation light to the facet of the light guide fiber bundle inside the endoscope.

In such light source unit, an optical fiber bundle is located throughout the path from the excitation light emitting device to an interface of the optical path merging device, for preventing attenuation of the excitation light, as well as for making the light source unit smaller in dimensions. In FIG. 10, which is a perspective view showing a main structure of the light source unit provided with such optical fiber bundle, the optical fiber bundle is designated by the numeral 41.

As shown in FIG. 10, a base portion of the optical fiber bundle 41 is detachably connected to a casing of the excitation light emitting device via a connector 41a. An end facet of the optical fiber bundle 41 is detachably connected to a square pillar-shaped lens barrel 42 via a connector 41b. The lens barrel 42 serves to hold a collimator lens 43 that converts the excitation light emitted from the end facet of the optical fiber bundle 41 into a collimated beam. The lens barrel 42 is fixed to a frame plate 44 such that an optical axis of the collimator lens 43 runs orthogonal to an optical axis of the optical system of the white light. In FIG. 10, a dash-dot line Ax designates the optical axis of the optical system that leads the white light from the white light emitting device to the facet of the light guide fiber bundle inside the endoscope. An end portion of the light guide fiber bundle inside the endoscope is, when connected to the light source unit, disposed at a left-hand side behind the frame plate 44 according to the orientation of FIG. 10, and a central axis of the end portion is coaxial with the optical axis Ax of the white light optical system.

The frame plate 44 is further provided with a stage 45 via a rack and pinion mechanism, and the stage 45 is provided with a dichroic mirror 46 that transmits the white light but reflects the excitation light. The stage 45 is driven in a forward and backward direction (leftward and rightward in FIG. 10) according to the selected observation mode. When the stage 45 is moved upon selecting the special observation mode, the dichroic mirror 46 comes to a position where the optical path of the white light and the optical path of the excitation light intersect each other (the state shown in FIG. 10). The dichroic mirror 46 is set with an inclination of 45 degrees with respect to the optical axis of the collimator lens 43, as well as with respect to the optical axis Ax of the white light optical system. Accordingly, the white light is transmitted straight through the dichroic mirror 46 thus to reach the facet of the light guide fiber bundle inside the endoscope, while the excitation light is reflected in a right angle by the dichroic mirror 46, to thereby reach the facet of the light guide fiber bundle inside the endoscope.

When merging the optical path of the white light and that of the excitation light with the dichroic mirror 46 as above, the optical axis of the collimator lens 43 after reflected by the dichroic mirror 46 has to coincide with the optical axis Ax of the white light optical system.

However, in the light source unit as shown in FIG. 10, once the lens barrel 42 is mounted on the frame plate 44, it is impossible to adjust an inclination or a position of the collimator lens 43 with respect to the optical axis Ax of the white light optical system.

The present invention has been conceived in view of the foregoing situation. The present invention is advantageous in that it provides an adjustment mechanism, to be used in a light source unit provided with an excitation light optical system that converts excitation light emitted by an excitation light emitting device into a collimated beam and emits such beam to an optical path merging device, which allows adjusting an inclination or a position of an optical axis of the excitation light optical system with respect to an optical axis of the white light optical system.

According to an aspect of the invention, there is provided an adjustment mechanism that adjusts an inclination and a position of an optical axis of an excitation light optical system with respect to an optical axis of a white light optical system, to be used in a light source unit including the white light optical system that leads white light emitted by a white light emitting device to a facet of a light guide provided inside an endoscope, the excitation light optical system that leads excitation light emitted by an excitation light emitting device, and an optical path merging device disposed on the optical axis of the white light optical system for bending the optical axis of the excitation light optical system substantially at a right angle toward the light guide, so as to supply the facet of the light guide with the white light for illuminating an internal area of a body cavity in which an insertion tube of the endoscope is inserted, and the excitation light for exciting a body tissue under a body cavity wall.

The adjustment mechanism includes a frame plate orthogonally placed with respect to the optical axis of the white light optical system, and perforated with a pair of circular holes the respective centers of which are aligned on a straight line perpendicular to a direction of the optical axis of the white light optical system, and an elliptical hole having a major axis coinciding with the straight line and a minor axis whose extension perpendicularly intersects with the optical axis of the white light optical system. The adjustment mechanism further includes a plate-shaped lever perforated with a first elliptical hole and a second elliptical hole, respective major axes of which are perpendicular to each other, and provided with a cylindrical projection located on an extension of a segment connecting the centers of the first elliptical hole and the second elliptical hole and rotatably and slidably fitted in the elliptical hole in the frame plate. The adjustment mechanism further includes a fixing unit that fixes the excitation light optical system to the plate-shaped lever such that the optical axis of the excitation light optical system becomes perpendicular to a direction parallel to the extension of the segment connecting the centers of the first and second elliptical holes.

Further, the adjustment mechanism includes a first adjuster including a first supporting axle rotatably held in one of the circular holes in the frame plate, and a first disc-shaped cam to which the first supporting axle is eccentrically fixed, the first disc-shaped cam being rotatably and slidably fitted in the first elliptical hole of the plate-shaped lever, and a second adjuster including a second supporting axle rotatably held in the other circular hole in the frame plate, and a second disc-shaped cam to which the second supporting axle is eccentrically fixed, the second disc-shaped cam being rotatably and slidably fitted in the second elliptical hole of the plate-shaped lever.

With this configuration, it is possible to adjust an inclination and a position of an optical axis of the excitation light optical system with respect to an optical axis of the white light optical system, in the light source unit provided with the excitation light optical system that converts the excitation light emitted by the excitation light emitting device into a collimated beam and emits the collimated beam to the optical path merging device.

Optionally, the adjustment mechanism may include a stage including a base seat which holds the optical path merging device, the stage having a first side surface to which the base seat is attached, and a second side surface facing the frame plate, a supporting member disposed with a predetermined gap from the frame plate, so as to support a first border portion of the stage, the stage being rotatable around an axis parallel to a segment connecting the centers of the pair of circular holes, and an angle adjuster that moves a second border portion of the stage opposite to the first border portion supported by the supporting member, so as to cause the second border portion to contact with or separate from the frame plate.

Still optionally, the first adjuster may have a first knob fixed to the first disc-shaped cam, and the second adjuster may have a second knob fixed to the second disc-shaped cam.

Still optionally, the major axis of the first elliptical hole of the plate-shaped lever may be parallel with the extension of the segment connecting the centers of the first and second elliptical holes of the plate-shaped lever so that, by rotating the first disc-shaped cam of the first adjuster manipulating the first knob, the plate-shaped lever is rotated around a center axis of the cylindrical projection.

Still optionally, the major axis of the second elliptical hole of the plate-shaped lever may be perpendicular to the extension of the segment connecting the centers of the first and second elliptical holes of the plate-shaped lever so that, by rotating the second disc-shaped cam of the second adjuster manipulating the second knob, the plate-shaped lever moves in parallel with the extension of the segment connecting the centers of the first and second elliptical holes.

Still optionally, the adjustment mechanism may include a first flanged screw capable of being screwed into the first supporting axle of the first adjuster so as to make the first adjuster press the plate-shaped lever against the frame plate, and a second flanged screw capable of being screwed into the second supporting axle of the second adjuster so as to make the second adjuster press the plate-shaped lever against the frame plate.

Still optionally, the adjustment mechanism may include a third flanged screw capable of being screwed into the cylindrical projection of the plate-shaped lever so that the plate-shaped lever is supported by the frame plate.

BRIEF DESCRIPTION OF THE ACCOMPANYING DRAWINGS

DETAILED DESCRIPTION OF THE EMBODIMENTS

Referring to the accompanying drawings, embodiments of the present invention will be described hereunder. In should be noted that the embodiment described below can be used with a light source unit provided in a generally available endoscope system.

Figure 1:
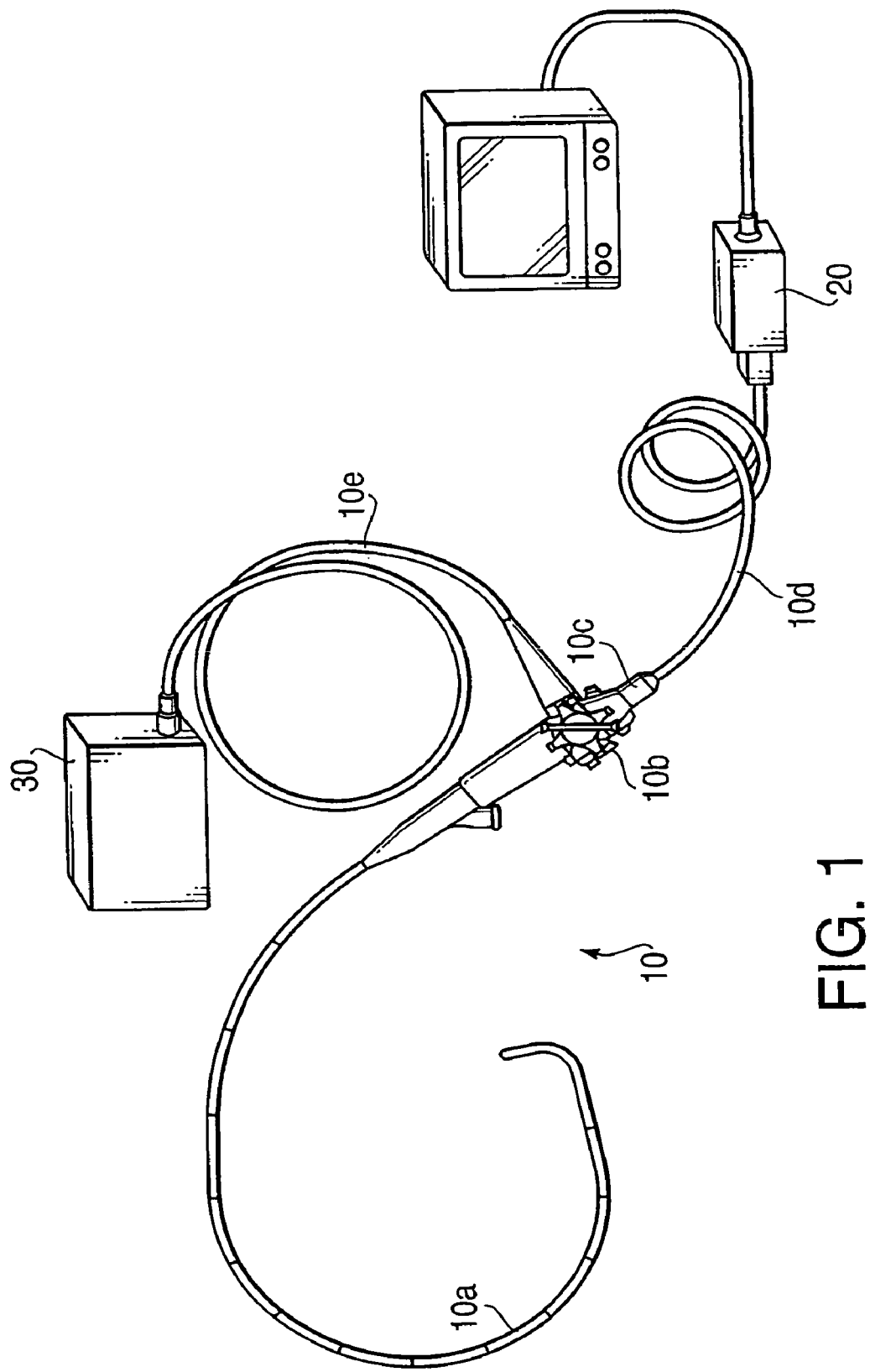
FIG. 1 is an illustration showing an appearance of an endoscope system to which the present invention is applied.

FIG. 1 is an illustration showing an appearance of an endoscope system to which the present invention is applied. As shown therein, the endoscope system includes an endoscope 10, an image processing unit 20, and a light source unit 30.

The endoscope 10 includes an insertion tube 10a of a slim and lengthy shape so as to be inserted into a body cavity, a manipulating unit 10b having an angle knob for remote manipulation of the insertion tube 10a, an imaging unit 10c for capturing an image of an object confronting a tip portion of the insertion tube 10a, a first cable 10d connecting the imaging unit 10c and the image processing unit 20, and a second cable 10e connecting the manipulating unit 10b and the light source unit 30.

The insertion tube 10a includes therein an objective optical system, which creates an image of an object confronting the tip portion of the insertion tube 10a. Such image is transmitted through an image guide fiber bundle extended through inside the insertion tube 10a, to a base portion thereof. The imaging unit 10c converts the object image transmitted to the base portion of the insertion tube 10a into image data, and outputs the image data to the image processing unit 20 via the first cable 10d. The image processing unit 20 executes a predetermined processing on the image data received, and has the object image displayed on a monitor screen based on the processed image data.

The endoscope 10 further includes a light guide fiber bundle. The light guide fiber bundle is extended throughout a section from the tip portion of the insertion tube 10a to the end portion of the second cable 10e, through inside the insertion tube 10a, manipulating unit 10b and the second cable 10e. The end portion of the second cable 10e is detachably connected to the light source unit 30, such that an end facet of the light guide fiber bundle is inserted into inside the light source unit 30. The light source unit 30 serves to introduce light to the end facet of the light guide fiber bundle. The light guide fiber bundle inside the endoscope 10 conducts the light emitted from the light source unit 30 to the tip portion of the insertion tube 10a, thus to emit the light therefrom.

Figure 2:
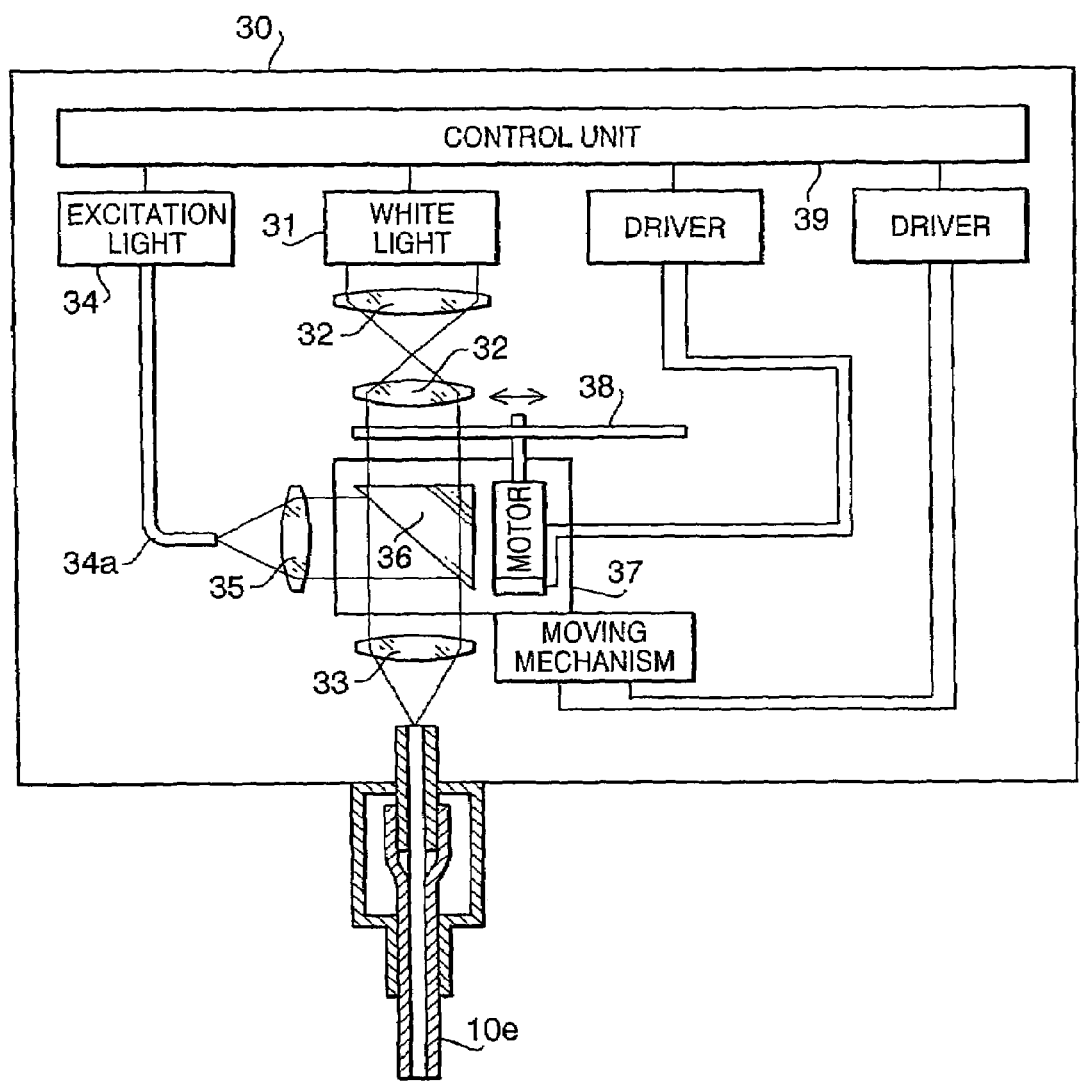
FIG. 2 is a block diagram showing a configuration of a light source unit of the endoscope system.

FIG. 2 is a block diagram showing a configuration of the light source unit 30. As shown therein, the light source unit 30 includes a white light emitting device 31 that emits a white collimated beam, an afocal optical system 32 that reduces the optical bundle diameter of the white light emitted by the white light emitting device 31, and a condenser lens 33 that converges the white light onto the end facet of the light guide fiber bundle inside the endoscope 10.

The light source unit 30 also includes an excitation light emitting device 34 that emits excitation light for exciting a body tissue under a body cavity wall, a collimator lens 35 that converts the excitation light emitted by the excitation light emitting device 34 into a collimated beam, and a dichroic mirror 36 that reflects the excitation light but transmits the white light. The excitation light emitting device 34 is provided with an optical fiber bundle 34a that conducts the excitation light to a focal point of the collimator lens 35. A central axis of the end facet of the optical fiber bundle 34a is coaxial with the optical axis of the collimator lens 35, and orthogonal to the optical axis of the afocal optical system 32 and the condenser lens 33. The dichroic mirror 36 is located on the stage 37, to serve as an optical path merging device.

The stage 37 is movable only in one direction orthogonal to the optical path of the white light, by a moving mechanism constituted of for example a rack and pinion engagement. On the stage 37, the dichroic mirror 36 is placed with an inclination of 45 degrees with respect to the optical axis of the collimator lens 35, as well as with respect to the optical axis of the afocal optical system 32 and the condenser lens 33.

When the stage 37 is driven in a forward and backward direction, the dichroic mirror 36 is either set to interfere with the optical path of the white light between the afocal optical system 32 and the condenser lens 33, or is removed from such optical path. When the dichroic mirror 36 is set to interfere with the optical path of the white light, the white light passes straight through the dichroic mirror 36 thus to reach the condenser lens 33, while the excitation light is reflected at a right angle by the dichroic mirror 36, to thereafter reach the condenser lens 33. Accordingly, both of the excitation light and the white light are converged by the condenser lens 33 onto the end facet of the light guide fiber bundle inside the endoscope. On the other hand, when the dichroic mirror 36 is removed from the optical path of the white light, only the white light can reach the condenser lens 33, to be thereby converged onto the end facet of the light guide fiber bundle inside the endoscope.

The light source unit 30 further includes a disc-shaped rotary shutter 38. The rotary shutter 38 is perforated with a generally sector-shaped through hole, and an apex of the generally sector shape coincides with the center of the disc (see FIG. 4). Also, a tip portion of a driving shaft of a motor is fixed to a central portion of the rotary shutter 38, such that the rotary shutter 38 is mounted on the stage 37. When the stage 37 moves so as to set the dichroic mirror 36 to interfere with the optical path of the white light, the rotary shutter 38 is also set to perpendicularly interfere with the optical path of the white light between the dichroic mirror 36 and the afocal optical system 32. Likewise, when the stage 37 moves so as to remove the dichroic mirror 36 from the optical path of the white light, the rotary shutter 38 is also removed from the optical path.

The stage 37 is thus driven by switching the observation mode. The observation modes include a basic observation mode of illuminating an object with the white light to perform ordinary observation, and a special observation mode of alternately irradiating the white light and the excitation light to the object, thus to perform special observation. Selection of such observation modes can be executed by a switch provided on the manipulating unit 10b of the endoscope 10, or on an operation panel of the light source unit 30. Such switch is connected to a control unit 39 that controls an entirety of the light source unit 30.

The control unit 39 drives the stage 37 so as to remove the dichroic mirror 36 and the rotary shutter 38 from the optical path of the white light when the basic observation mode is selected. Accordingly in the basic observation mode, only the white light is introduced to the end facet of the light guide fiber bundle inside the endoscope 10. In this case, an internal area of the body cavity, where the insertion tube 10a of the endoscope 10 is inserted, is illuminated exclusively by the white light emitted from the tip portion of the insertion tube 10a.

By contrast, when the special observation mode is selected, the control unit 39 drives the stage 37 so as to set the dichroic mirror 36 and the rotary shutter 38 to interfere with the optical path of the white light. The control unit 39 also rotates the rotary shutter 38 so as to introduce the white light to the end facet of the light guide fiber bundle inside the endoscope 10 at a predetermined time interval, and controls the excitation light emitting device 34 to blink so as to emit the excitation light at a moment that the white light is not introduced to the light guide fiber bundle. Employing for example a laser diode to constitute the excitation light emitting device 34 allows performing such blink control. Thus in the special observation mode, the white light and the excitation light are alternately introduced to the end facet of the light guide fiber bundle inside the endoscope 10. Consequently, in the body cavity where the insertion tube 10a of the endoscope is inserted, reflection of the white light at a surface of the body cavity wall and emission of fluorescence by the body tissue under the body cavity wall are alternately repeated.

Figure 3:
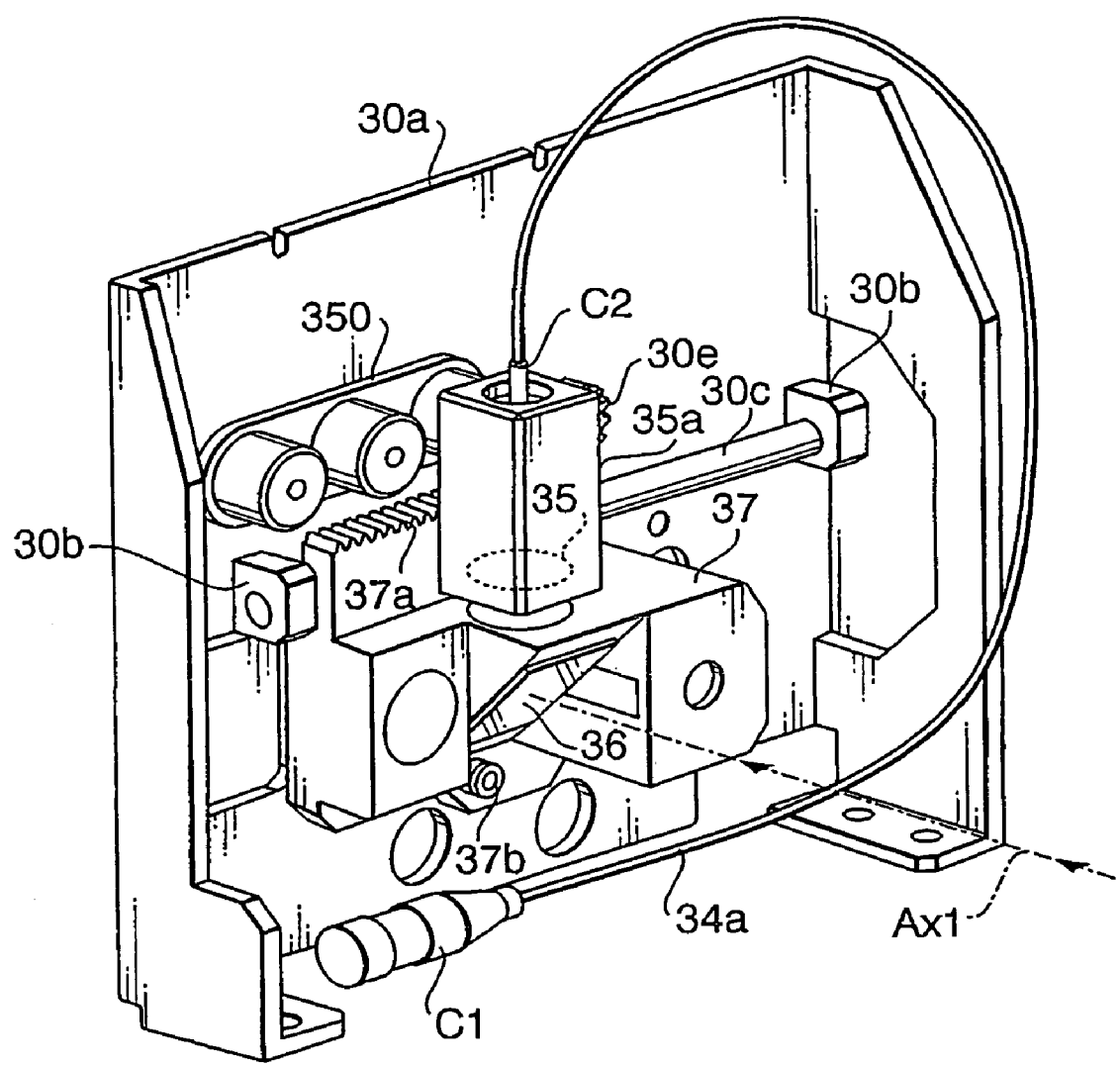
FIG. 3 is a perspective view showing a main structure of the light source unit including an adjustment mechanism according to an embodiment of the present invention.
Figure 4:
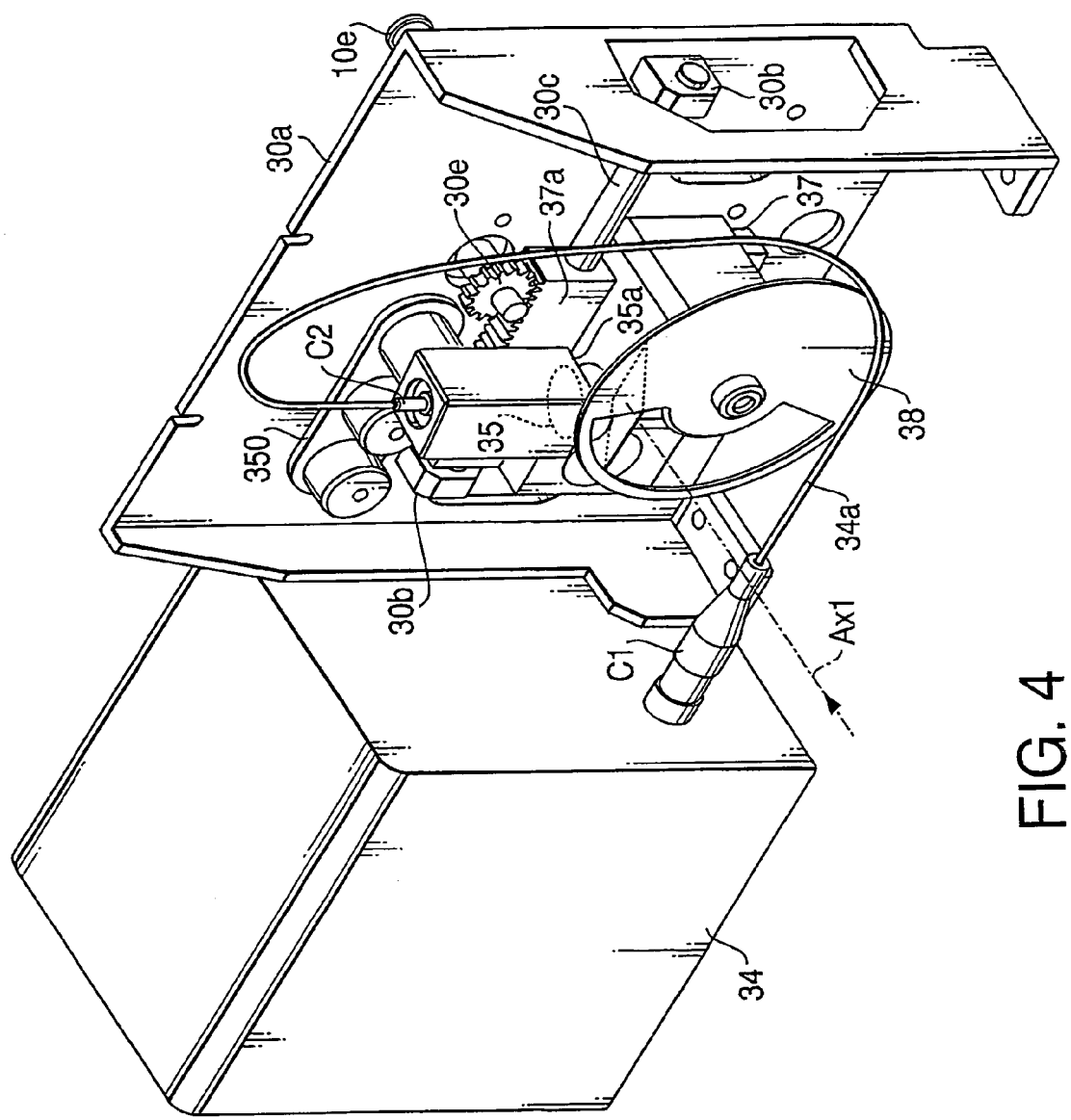
FIG. 4 is a perspective view showing the main structure of the light source unit including the adjustment mechanism.

FIGS. 3 and 4 are perspective views showing a main structure of the light source unit 30 including an adjustment mechanism according to the present invention. In FIG. 3, the rotary shutter 38 and the motor therefor are omitted. Also, FIG. 5 is a side view of the light source unit 30, viewed from the right according to the orientation of FIG. 3.

Figure 5:
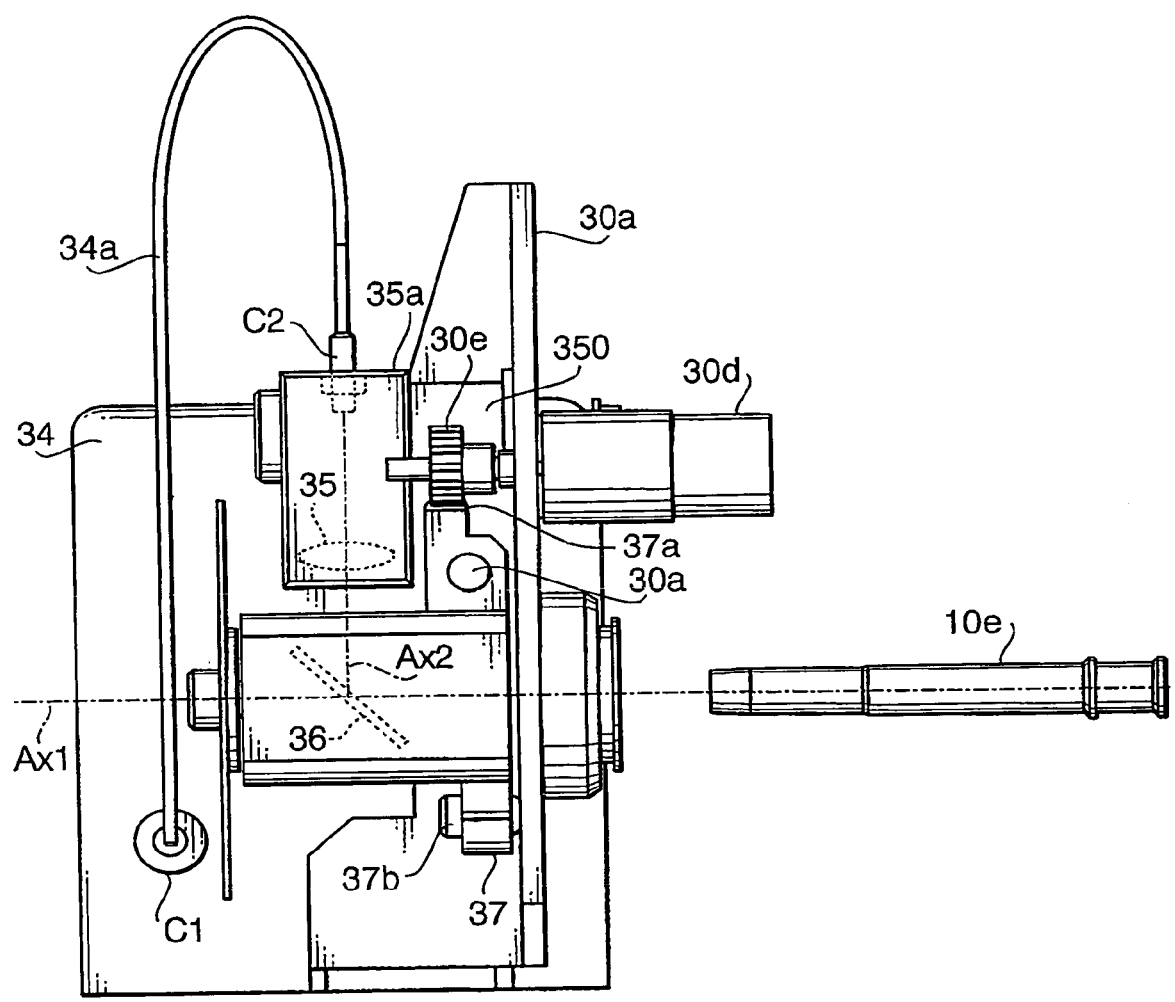
FIG. 5 is a side view showing the light source unit viewed from the right according to orientation of FIG. 3.

According to FIGS. 3 to 5, the base portion of the optical fiber bundle 34a is connected to a generally parallelepiped-shaped casing of the excitation light emitting device 34, via a connector C1. The end facet of the optical fiber bundle 34a is detachably connected to a square pillar-shaped lens barrel 35a via a connector C2. The lens barrel 35a serves to hold the collimator lens 35 for the excitation light, and is fixed to the frame plate 30a, which is vertically erected, via an adjustment mechanism 350 according to the embodiment of the present invention, to be subsequently described. Here, the white light emitting device 31 is located at a closer right-hand side according to the orientation of FIG. 3, while the tip portion of the second cable 10e of endoscope 10 is located at a farther left-hand side in FIG. 3. The central axis of the light guide fiber bundle inside the second cable 10e is coaxial with the optical axis Ax1, which runs orthogonal to the frame plate 30a. The lens barrel 35a fixed to the frame plate 30a is oriented such that the optical axis Ax2 of the collimator lens 35 runs orthogonal to the optical axis Ax1, as well as vertical.

The frame plate 30a also sustains end portions of a horizontal bar 30c disposed with a predetermined gap therefrom, via a pair of supporting blocks 30b, 30b protruding from the wall thereof toward the lens barrel 35a. The horizontal bar 30c is torsionally oriented with respect to the optical axis Ax1. The horizontal bar 30c is also engaged with the stage 37. The stage 37 is formed such that base seats for a motor that rotates the rotary shutter 38 and for the dichroic mirror 36 protrude from one side of a base plate. The stage 37 is perforated with a through hole along a border portion thereof. The through hole is oriented parallel to the border portion, and has an inner diameter substantially the same as the diameter of the horizontal bar 30c (more precisely, slightly larger). The stage 37 is hung from the horizontal bar 30c penetrating the through hole, with a plane side wall thereof opposite to the base seats facing the wall of the frame plate 30a. In this state, a border portion of the stage 37 opposite to the through hole, i.e. the lower border portion, is in contact with the frame plate 30a. Further, on an entirety of the upper border portion of the stage 37, inside which the horizontal bar 30c is located, a rack gear 37a is provided, which is engaged with a pinion gear 30e attached to the driving shaft of a motor 30d mounted on the frame plate 30a.

When the motor 30d rotates in a forward and backward direction, the stage 37 is moved forward and backward (left and right according to FIG. 3, perpendicularly back and forth with respect to FIG. 5) along the horizontal bar 30c. When the stage 37 is moved upon selecting the special observation mode, the dichroic mirror 36 comes to a position where the optical path of the excitation light and that of the white light intersect each other (the state shown in FIGS. 3 and 4). The dichroic mirror 36 is set with an inclination of 45 degrees with respect to the optical axis of the collimator lens 43, as well as with respect to the optical axis Ax of the white light optical system, as stated earlier. Accordingly, the white light emitted from the afocal optical system 32 is transmitted straight through the dichroic mirror 36 thus to reach the condenser lens 33, while the excitation light emitted from the collimator lens 35 is reflected at a right angle by the dichroic mirror 36, to thereby reach the condenser lens 33. Accordingly, both the white light and the excitation light can be introduced to the end facet of the light guide fiber bundle inside the endoscope 10.

The stage 37 is provided with a screw hole perpendicularly oriented thereto near a lower lateral edge thereof, into which a screw 37b is inserted toward the frame plate 30a, as shown in FIGS. 3 and 5. As the screw 37b is screwed deeper into the screw hole, a tip portion of the screw 37b projects from the flat plate of the stage 37 facing the frame plate 30a, until finally contacting with the frame plate 30a. The projecting length of the tip portion of the screw 37b can be adjusted according to a screwing depth thereof. Adjusting thus the projecting length of the tip portion of the screw 37b causes the stage 37 to rotate around the central axis of the horizontal bar 30c, thereby varying a distance between the lower edge of the stage 37 and the frame plate 30a. This causes a variation in inclination of the dichroic mirror 36 with respect to the optical axis Ax1 of the afocal optical system 32 and the condenser lens 33. In a word, the screw 37b serves as an adjustment mechanism of an inclination of the dichroic mirror 36.

Figure 6:
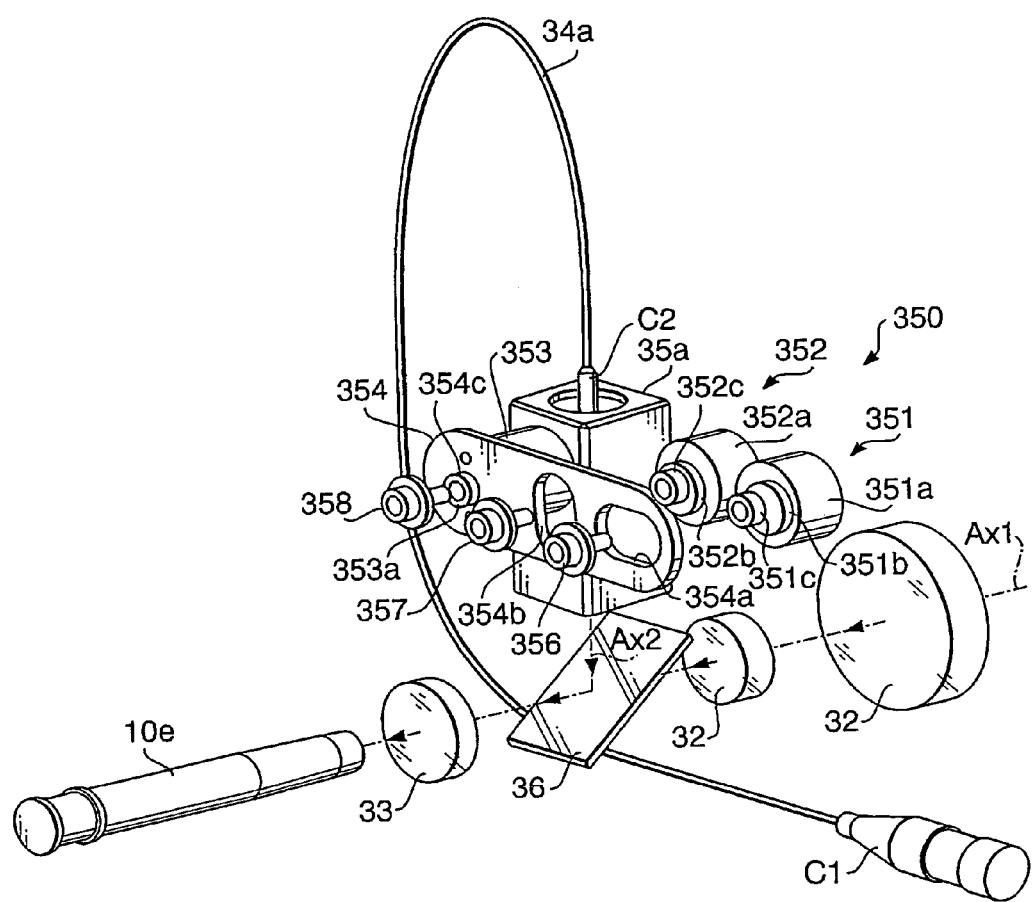
FIG. 6 is an exploded perspective view showing a part of the light source unit including the adjustment mechanism.
Figure 7:
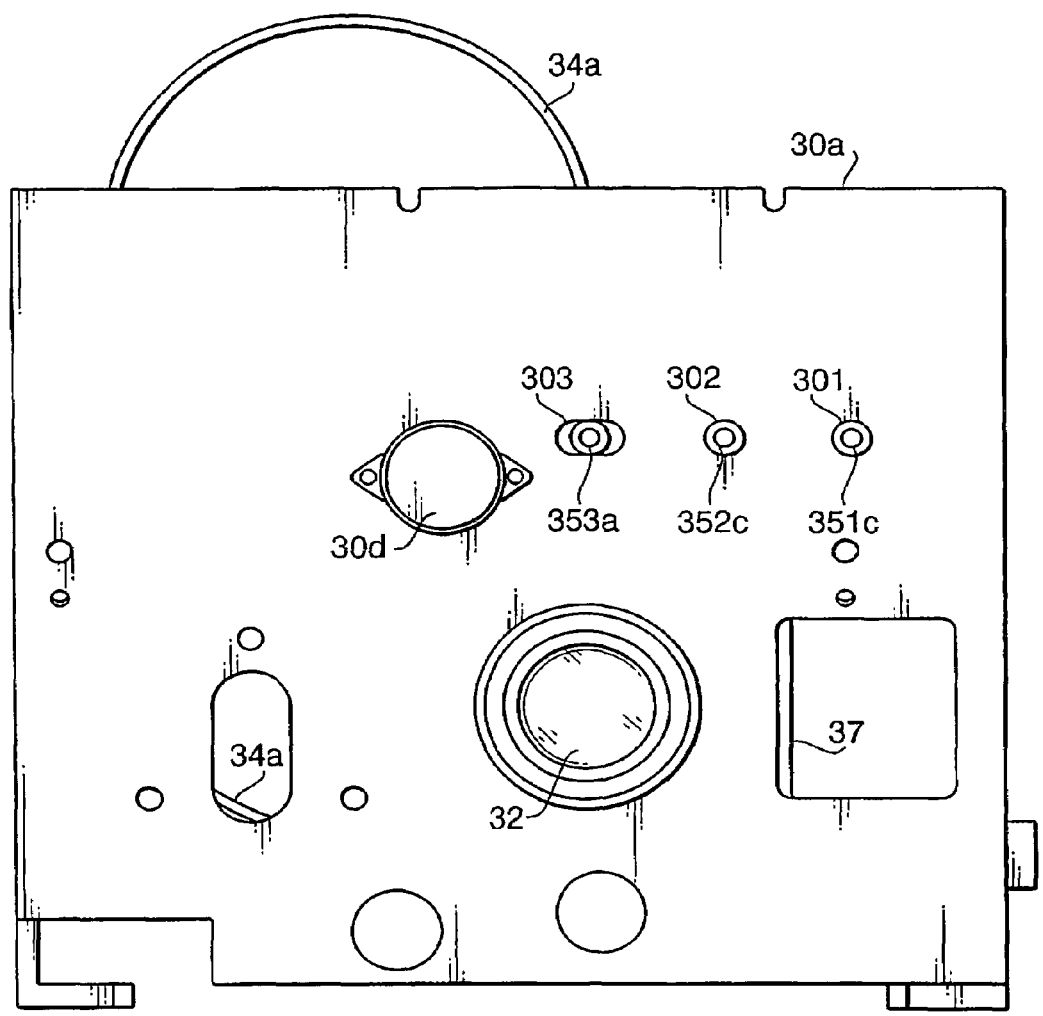
FIG. 7 is a rear view showing the light source unit including the adjustment mechanism.

FIG. 6 is an exploded perspective view showing only the respective optical systems and the adjustment mechanism 350 according to the embodiment of the present invention, out of the components of the light source unit 30. FIG. 7 is a rear view of the frame plate 30a, viewed from the side where the connection box of the second cable 10e is located.

The adjustment mechanism 350 includes a first adjuster 351, a second adjuster 352, a supporting member 353, and a lever plate 354. The first adjuster 351, the second adjuster 352, and the supporting member 353 are intended for pressing the lever plate 354 against the frame plate 30a. The supporting member 353 also serves as the fixture for the lens barrel 35a accommodating the collimator lens 35 for the excitation light, with respect to the frame plate 30a. The adjustment mechanism 350 will be described in further details hereunder.

The first adjuster 351 includes a column-shaped knob 351a constituting the main portion thereof. The knob 351a is provided with a disc-shaped cam plate 351b having a smaller diameter than the knob 351a, integrally formed so as to project from a bottom face thereof. Further, the cam plate 351b is provided with a cylindrical projection 351c having a still smaller diameter, integrally formed so as to project therefrom. In a word, the first adjuster 351 is a circular column with two levels of stepped projections on a bottom face thereof, as a whole. Here, the central axis of the knob 351a and that of the cylindrical projection 351c are mutually coaxial, while the cam plate 351b is eccentrically formed with respect to these central axes. The cylindrical projection 351c has a projecting length that is slightly shorter than the thickness of the frame plate 30a, and is provided with a female-threaded bore, so as to serve as a screw hole.

The second adjuster 352 is formed in the same shape and dimensions as those of the first adjuster 351. Specifically, the second adjuster 352 includes a column-shaped knob 352a as the main body, a cam plate 352b eccentrically formed with respect thereto, a cylindrical projection 352c coaxial with the knob 352a. The cylindrical projection 352c has a projecting length that is slightly shorter than the thickness of the frame plate 30a, and is provided with a female-threaded bore.

The supporting member 353 is also of a column shape. The supporting member 353 is provided with a coaxial cylindrical projection 353a having a smaller diameter, integrally formed on a bottom face thereof. The cylindrical projection 353a has a projecting length that is slightly shorter than the thickness of the frame plate 30a, and is provided with a female-threaded bore, so as to serve as a screw hole.

The lever plate 354 is an elliptical plate, having a thickness equal to the height of the cam plate 351b, 352b of the first adjuster 351 and the second adjuster 352. The lever plate 354 is perforated with a pair of elliptical holes 354a, 354b and a through hole 354c, such that the respective centers of the elliptical holes 354a, 354b and of the through hole 354c are aligned along the major axis of the lever plate 354.

As used herein, the term "elliptical" hole, plate or etc. includes an oblong shape made by elongating a circular shape as well as an ellipse. Similarly to an ellipse, the major axis of the oblong (circular) shape is defined as an axis extending in an elongated direction and including a center thereof, and the minor axis of the oblong (circular) shape is defined as an axis extending in a direction perpendicular to the elongated direction and including the center thereof.

The minor axis of the first elliptical hole 354a is orthogonal to the major axis of the lever plate 354. The length of the minor axis of the first elliptical hole 354a is substantially the same as the diameter of the cam plate 351b on the first adjuster 351 (more precisely, slightly larger). Accordingly, upon fitting the cam plate 351b of the first adjuster 351 into the first elliptical hole 354a, the cam plate 351b can be made to rotate within the first elliptical hole 354a, as well as to slide along the major axis of the first elliptical hole 354a.

The second elliptical hole 354b is formed in the same shape and dimensions as those of the first elliptical hole 354a. Accordingly, upon fitting the cam plate 352b of the second adjuster 352 into the second elliptical hole 354b, the cam plate 352b can be made to rotate within the second elliptical hole 354b, as well as to slide along the major axis of the second elliptical hole 354b. Here, the minor axis of the second elliptical hole 354b coincides with the major axis of the lever plate 354, and hence the direction of the major axis of the second elliptical hole 354b is perpendicular to the direction of the major axis of the first elliptical hole 354a.

The through hole 354c is of a circular shape, with a diameter that is substantially the same as that of the cylindrical projection 353a of the supporting member 353 (more precisely, slightly larger). The through hole 354c is located opposite to the first elliptical hole 354a, across the second elliptical hole 354b.

The supporting member 353 is fixed to the lever plate 354, with the cylindrical projection 353a inserted into the through hole 354c of the lever plate 354. Here, the supporting member 353 is unmovably fixed to the lever plate 354 (i.e. unable to rotate with respect to the lever plate 354), for example via a mortise and tenon joint or bonding with an adhesive. Also, the supporting member 353 is fixed to the lens barrel 35a, with the other bottom face thereof, i.e. opposite to the face where the cylindrical projection 353a is provided, butted to a side wall of the lens barrel 35a accommodating the collimator lens 35 for the excitation light. In this state, the optical axis Ax2 of the collimator lens 35 is perpendicular to the direction of the major axis of the lever plate 354, and is torsionally oriented with respect to the same major axis.

Under the foregoing structure of lever plate 354 and the lens barrel 35a with respect to the supporting member 353, the cylindrical projection 353a of the supporting member 353 constitutes a cylindrical projection protruding from the surface of the lever plate 354. The cylindrical projection 353a protruding from the lever plate 354 is inserted into the elliptical hole 303 provided in the frame plate 30a, as shown in FIG. 7. The direction of the major axis of the elliptical hole 303 is parallel to the horizontal bar 30c, and an extension of the minor axis thereof perpendicularly intersects with the optical axis Ax1. Also, the length of the minor axis the elliptical hole 303 is substantially the same as the diameter of the cylindrical projection 353a of the supporting member 353 (more precisely, slightly longer). Accordingly, upon inserting the portion of the cylindrical projection 353a protruding from the lever plate 354 into the elliptical hole 303, the cylindrical projection 353a can be made to rotate within the elliptical hole 303, as well as to slide along the major axis of the elliptical hole 303, i.e. in a horizontal direction. Fastening the cylindrical projection 353a inserted into the elliptical hole 303 with a third flanged screw 358, the lever plate 354 and the lens barrel 35a attached to the supporting member 353 are supported by the frame plate 30a.

Referring further to FIG. 7, the frame plate 30a is perforated with a pair of circular holes 301, 302 in addition to the elliptical hole 303. The diameter of these circular holes 301, 302 is substantially the same as that of the cylindrical projection 351c of the first adjuster 351, i.e. substantially the same as that of the cylindrical projection 352c of the second adjuster 352 (more precisely, slightly larger). In addition, the respective centers of the circular holes 301, 302 are aligned in a direction parallel to the horizontal bar 30c, together with the center of the elliptical hole 303.

The first circular hole 301 receives the cylindrical projection 351c of the first adjuster 351, which has its cam plate 351b inserted to the first elliptical hole 354a of the lever plate 354. Then, a first flanged screw 356 is screwed into the cylindrical projection 351c inserted to the first circular hole 301, thus to make the first adjuster 351 press the lever plate 354 against the frame plate 30a.

Likewise the circular hole 302, located between the first circular hole 301 and the elliptical hole 303, receives the cylindrical projection 352c of the second adjuster 352, which has its cam plate 352b inserted to the second elliptical hole 354b of the lever plate 354. Then, a second flanged screw 357 is screwed into the cylindrical projection 352c inserted to the second circular hole 302, thus to make the second adjuster 352 press the lever plate 354 against the frame plate 30a.

The adjustment mechanism 350 thus constructed operates as described below. Here, FIGS. 8 and 9 are perspective views of the adjustment mechanism 350 and the respective optical systems, viewed from different angles from FIG. 6.

In the event that, upon completing the assembly of the light source unit 30 or receipt of a repair request therefor, the optical axis Ax2 of the collimator lens 35 serving as the optical system for the excitation light has proved to be not coaxial with the optical axis Ax1 of the afocal optical system 32 and the condenser lens 33 in the section beyond the dichroic mirror 36, an operator can utilize the adjustment mechanism 350 to adjust a position and orientation of the optical axis Ax2. Specifically, the operator can slightly loosen the flanged screws 356 to 358, and manipulate the knob 351a of the first adjuster 351 and the knob 352a of the second adjuster 352, so as to adjust a position and orientation of the optical axis Ax2.

Figure 8:
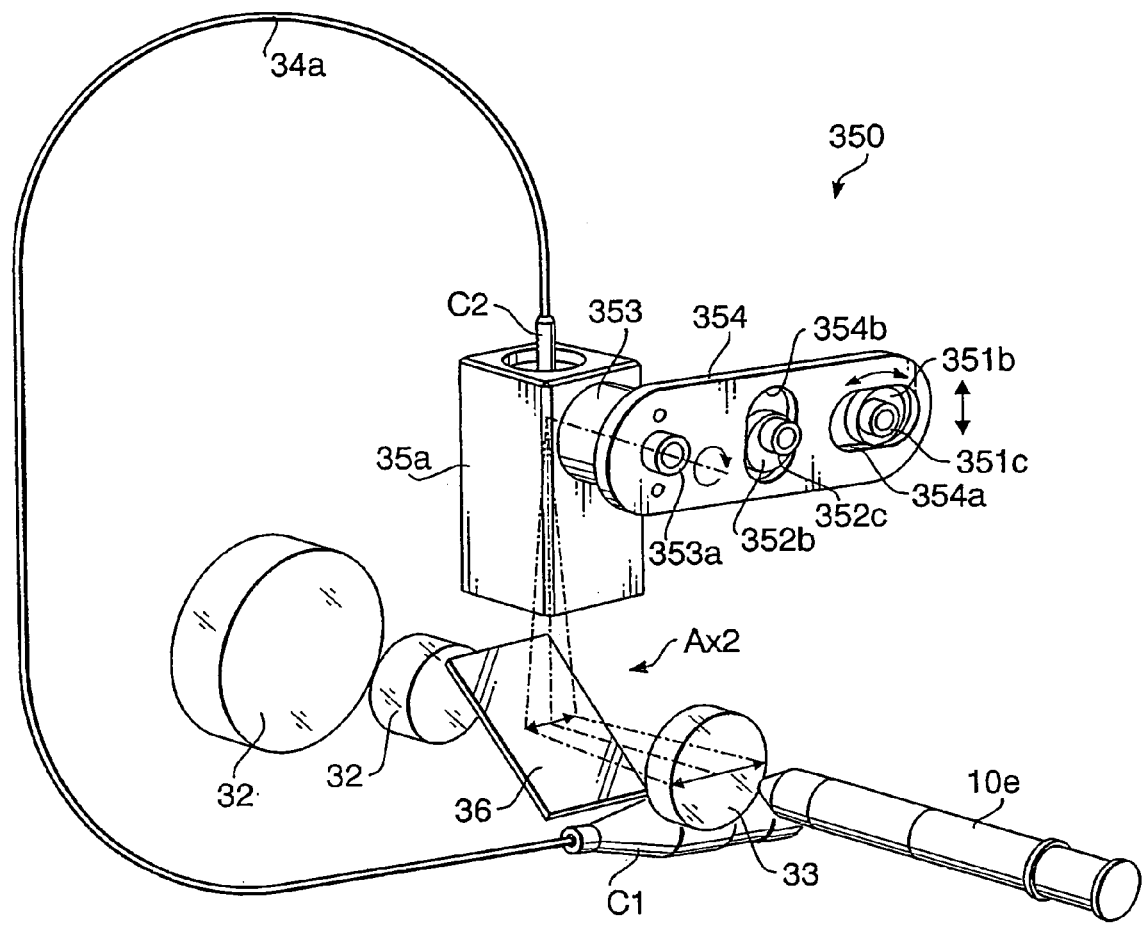
FIG. 8 is a fragmentary perspective view for explaining a movement of an optical axis of a collimator lens caused by manipulation of a first adjuster.

FIG. 8 is a fragmentary perspective view for explaining a movement of the optical axis Ax2 caused by manipulation of the first adjuster 351. When the operator holds and rotates the knob 351a of the first adjuster 351, the cam plate 351b of the first adjuster 351 performs an eccentric rotation inside the first elliptical hole 354a of the lever plate 354, so as to push the first elliptical hole 354a upward or downward parallel to the frame plate 30a. At this stage, since the cam plate 352b of the second adjuster 352 is rotatable and slidable within the second elliptical hole 354b, the lever plate 354 is caused to rotate around the central axis of the supporting member 353. Accordingly, the optical axis Ax2 of the collimator lens 35, which is fixed to the lever plate 354 via the supporting member 353 and the lens barrel 35a, also rotates around the central axis of the supporting member 353, thus to vary an inclination of the optical axis Ax2 with respect to the vertical. Since the optical axis Ax2 corresponds to the section bent by the dichroic mirror 36, such variation in inclination with respect to the vertical is equivalent to a variation in inclination with respect to the optical axis Ax1. In this way, the operator can adjust an inclination of the optical axis Ax2 with respect to the optical axis Ax1, by manipulating the first adjuster 351.

Figure 9:
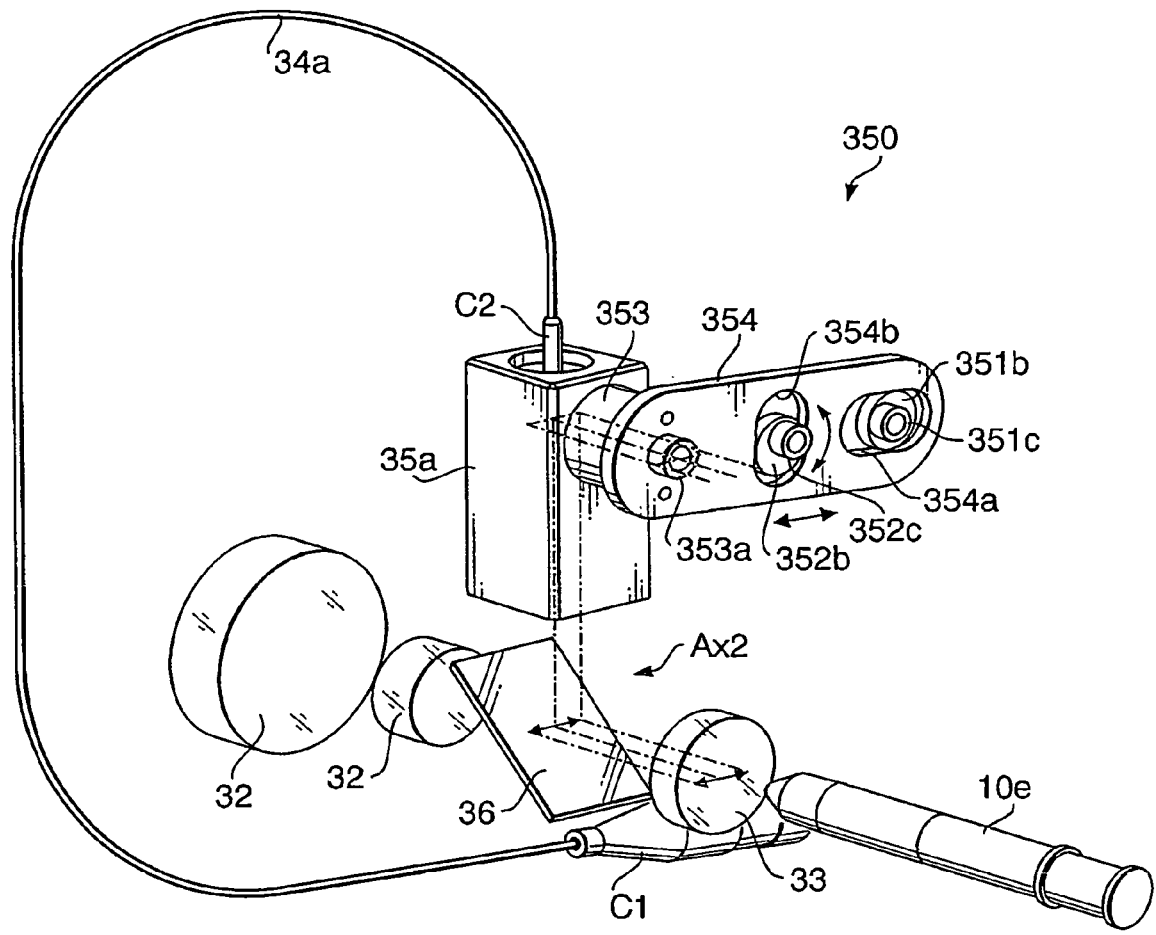
FIG. 9 is a fragmentary perspective view for explaining a movement of the optical axis of the collimator lens caused by manipulation of a second adjuster.
Figure 10:
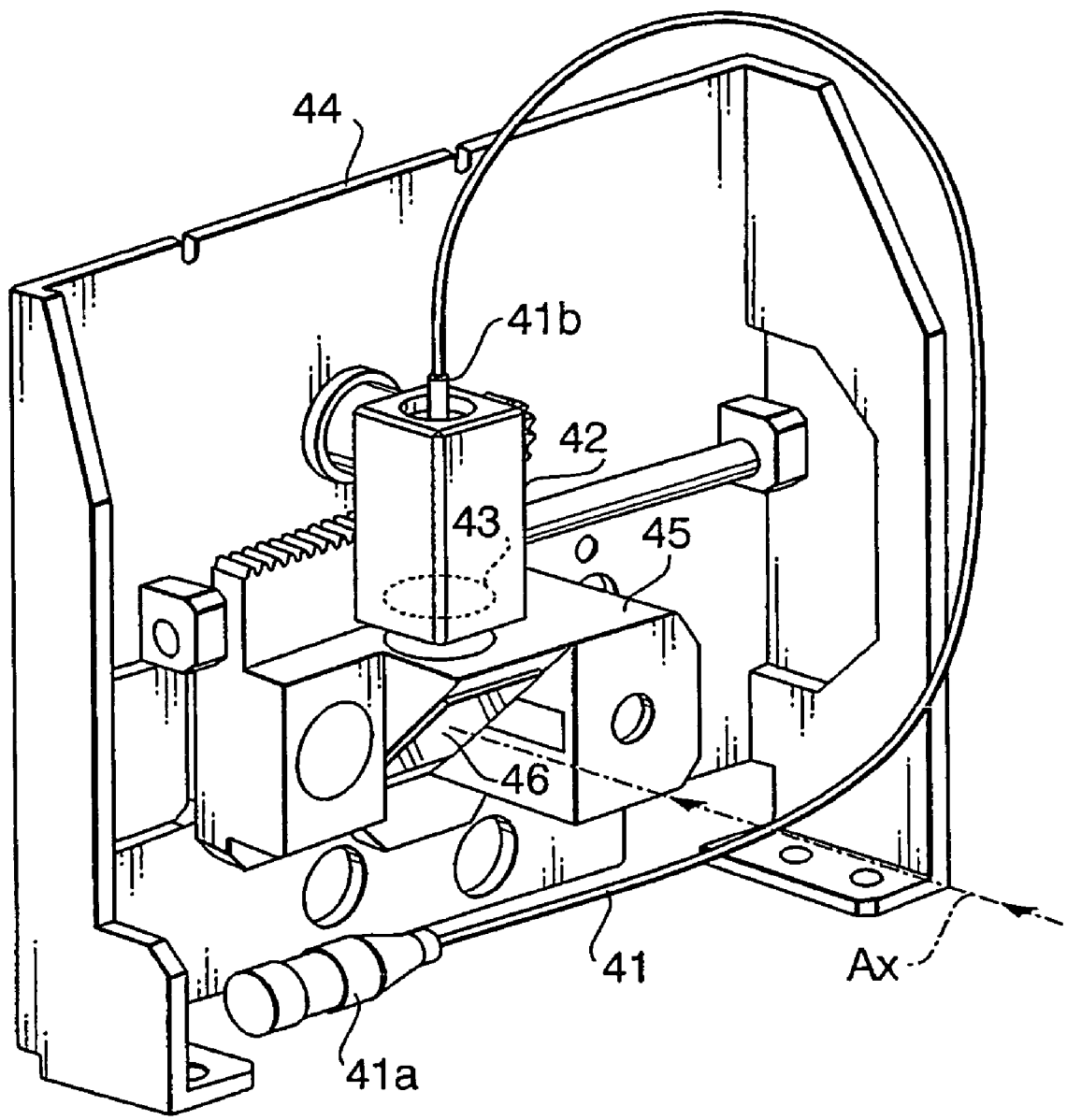
FIG. 10 is a perspective view showing a main structure of a conventional light source unit.

FIG. 9 is a fragmentary perspective view for explaining a movement of the optical axis Ax2 caused by manipulation of the second adjuster 352. When the operator holds and rotates the knob 352*a* of the second adjuster 352, the cam plate 352*b* of the second adjuster 352 performs an eccentric rotation inside the second elliptical hole 354*b* of the lever plate 354, so as to push the second elliptical hole 354*b* leftward or rightward according to the orientation of FIG. 9, parallel to the frame plate 30*a*. At this stage, since the cylindrical projection 353*a* of the supporting member 353 is rotatable and slidable within the elliptical hole 303 of the frame plate 30*a*, the central axis of the supporting member 353 is parallelly displaced in a horizontal direction. Besides, since the cam plate 351*b* of the first adjuster 351 is rotatable and slidable within the first elliptical hole 354*a*, the lever plate 354 is also parallelly displaced in a horizontal direction, while maintaining the current inclination with respect to the horizontal. Accordingly, the optical axis Ax2 of the collimator lens 35, which is fixed to the lever plate 354 via the supporting member 353 and the lens barrel 35*a*, is also parallelly displaced in a horizontal direction. Since the optical axis Ax2 corresponds to the section bent by the dichroic mirror 36, such parallel displacement in a horizontal direction is equivalent to a variation in distance from the optical axis Ax1. In this way, the operator can adjust a position of the optical axis Ax2 with respect to the optical axis Ax1, by manipulating the second adjuster 352.

In addition, changing a screwing depth of the screw 37*b* disposed in the lower border portion of the stage 37 causes a variation in inclination of the dichroic mirror 36 with respect to the optical axis Ax1, as stated earlier. Accordingly, the operator can adjust an elevation angle or a depression angle of the optical axis Ax2 with respect to the optical axis Ax1, by adjusting a screwing depth of the screw 37*b*.

In the adjustment mechanism 350 thus constructed, when the cam 351*b* of the first adjuster 351 is rotated, this cam 351*b* pushes the elliptical hole 354*a* of the lever plate 354 upward or downward parallel to the frame plate 30*a*, while allowing the cam 352*b* of the second adjuster 352 to rotate and slide inside the elliptical hole 354*b* of the lever plate 354. This causes the lever plate 354 to rotate around a central axis of the cylindrical projection, which in turn causes the optical axis Ax2 of an excitation light optical system (i.e. the collimator lens 35) to rotate around the central axis thereof. Such rotation creates a change in inclination of the optical axis of the excitation light optical system with respect to the optical axis of the white light optical system, in a section beyond an optical path merging device (i.e. the dichroic mirror 36). Accordingly, manipulating the first adjuster 351 enables adjusting an inclination of the optical axis of the excitation light optical system, with respect to the optical axis of the white light optical system.

Likewise, when the cam 352*b* of the second adjuster 352 is rotated, the cam 352*b* pushes the elliptical hole 354*b* of the lever plate 354 leftward or rightward parallel to the frame plate 30*a*, while allowing the cylindrical projection 353*a* of the lever plate 354 to rotate and slide inside the elliptical hole 303 of the frame plate 30*a*, and also the cam 351*b* of the first adjuster 351 to rotate and slide inside the elliptical hole 354*a* of the lever plate 354. This causes the lever plate 354 to be parallelly displaced along a direction of the major axis of the elliptical hole 354*a* of the frame plate, and hence the central axis of the cylindrical projection 353*a* of the lever plate 354 is also parallelly displaced in the same direction, which in turn causes a parallel displacement of the optical axis Ax2 of the excitation light optical system, again in the same direction. Such parallel displacement creates a change in distance of the optical axis Ax2 of the excitation light optical system from the optical axis of the white light optical system, in a section beyond the optical path merging device. Accordingly, manipulating the second adjuster 352 enables adjusting a position of the optical axis of the excitation light optical system with respect to the optical axis of the white light optical system.

As described above, the adjustment mechanism 350 according to the embodiment of the present invention allows adjusting an inclination or a position of an optical axis Ax2 of a collimator lens 35 with respect to an optical axis Ax1 of a white light optical system, in the light source unit 30 provided with the collimator lens 35 that converts the excitation light emitted by an excitation light emitting device 34 into a collimated beam and emits such beam to a dichroic mirror 36.

Although the present invention has been described in considerable detail with reference to certain preferred embodiments thereof, other embodiments are possible.

For example, the elliptical shape of each of the elliptical holes 303, 354*a*, and 354*b* may be replaced with various types of oblong shapes made by elongating a square shape or a circular shape.

The first adjuster 351 and the second adjuster 352 may be configured to have a groove (slot) or a hole such as a cross recess, a hexagonal or star socket, in which a screwdriver tip can be inserted so that the first and the second adjusters can be rotated by the screwdriver.

The present disclosure relates to the subject matter contained in Japanese Patent Application No. 2004-062043, filed on Mar. 5, 2004, which is expressly incorporated herein by reference in its entirety.

What is claimed is:

1. An adjustment mechanism that adjusts an inclination and a position of an optical axis of an excitation light optical system with respect to an optical axis of a white light optical system, to be used in a light source unit including the white light optical system that leads white light emitted by a white light emitting device to a facet of a light guide provided inside an endoscope, the excitation light optical system that leads excitation light emitted by an excitation light emitting device, and an optical path merging device disposed on the optical axis of the white light optical system for bending the optical axis of the excitation light optical system substantially at a right angle toward the light guide, so as to supply the facet of the light guide with the white light for illuminating an internal area of a body cavity in which an insertion tube of the endoscope is inserted, and the excitation light for exciting a body tissue under a body cavity wall, comprising:

a frame plate orthogonally placed with respect to the optical axis of the white light optical system, and perforated with a pair of circular holes the respective centers of which are aligned on a straight line perpendicular to a direction of the optical axis of the white light optical system, and an elliptical hole having a major axis coinciding with the straight line and a minor axis whose extension perpendicularly intersects with the optical axis of the white light optical system;

a plate-shaped lever perforated with a first elliptical hole and a second elliptical hole respective major axes of which are perpendicular to each other, and provided with a cylindrical projection located on an extension of a segment connecting centers of the first elliptical hole and the second elliptical hole and rotatably and slidably fitted in the elliptical hole in the frame plate;

a fixing unit that fixes the excitation light optical system to the plate-shaped lever such that the optical axis of the excitation light optical system becomes perpendicular to a direction parallel to the extension of the segment connecting the centers of the first and second elliptical holes;

a first adjuster including a first supporting axle rotatably held in one of the circular holes in the frame plate, and a first disc-shaped cam to which the first supporting axle is eccentrically fixed, the first disc-shaped cam being rotatably and slidably fitted in the first elliptical hole of the plate-shaped lever; and a second adjuster including a second supporting axle rotatably held in the other circular hole in the frame plate, and a second disc-shaped cam to which the second supporting axle is eccentrically fixed, the second disc-shaped cam being rotatably and slidably fitted in the second elliptical hole of the plate-shaped lever.

2. The adjustment mechanism according to claim 1, further comprising:

a stage including a base seat which holds the optical path merging device, the stage having a first side surface to which the base seat is attached, and a second side surface facing the frame plate;

a supporting member disposed with a predetermined gap from the frame plate, so as to support a first border portion of the stage, the stage being rotatable around an axis parallel to a segment connecting the centers of the pair of circular holes; and an angle adjuster that moves a second border portion of the stage opposite to the first border portion supported by the supporting member, so as to cause the second border portion to contact with or separate from the frame plate.

3. The adjustment mechanism according to claim 1, wherein the first adjuster has a first knob fixed to the first disc-shaped cam, and wherein the second adjuster has a second knob fixed to the second disc-shaped cam.

4. The adjustment mechanism according to claim 3, wherein the major axis of the first elliptical hole of the plate-shaped lever is parallel with the extension of the segment connecting the centers of the first and second elliptical holes of the plate-shaped lever so that, by rotating the first disc-shaped cam of the first adjuster manipulating the first knob, the plate-shaped lever is rotated around a center axis of the cylindrical projection.

5. The adjustment mechanism according to claim 3, wherein the major axis of the second elliptical hole of the plate-shaped lever is perpendicular to the extension of the segment connecting the centers of the first and second elliptical holes of the plate-shaped lever so that, by rotating the second disc-shaped cam of the second adjuster manipulating the second knob, the plate-shaped lever moves in parallel with the extension of the segment connecting the centers of the first and second elliptical holes.

6. The adjustment mechanism according to claim 1, further comprising:

a first flanged screw capable of being screwed into the first supporting axle of the first adjuster so as to make the first adjuster press the plate-shaped lever against the frame plate; and a second flanged screw capable of being screwed into the second supporting axle of the second adjuster so as to make the second adjuster press the plate-shaped lever against the frame plate.

7. The adjustment mechanism according to claim 1, further comprising a third flanged screw capable of being screwed into the cylindrical projection of the plate-shaped lever so that the plate-shaped lever is supported by the frame plate.

* * * * *